United States Patent
Bongers

(10) Patent No.: US 9,561,319 B2
(45) Date of Patent: Feb. 7, 2017

(54) DEVICE AND METHOD FOR FIXING A SEGMENT OF TUBING, FOR AN ARRANGEMENT FOR MONITORING AN ACCESS TO A PATIENT

(75) Inventor: Alexander Bongers, Langen (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 441 days.

(21) Appl. No.: 13/565,942

(22) Filed: Aug. 3, 2012

(65) Prior Publication Data

US 2013/0035627 A1    Feb. 7, 2013

Related U.S. Application Data

(60) Provisional application No. 61/514,912, filed on Aug. 4, 2011.

(30) Foreign Application Priority Data

Aug. 4, 2011  (DE) .......................... 10 2011 109 378

(51) Int. Cl.
    *A61M 37/00*    (2006.01)
    *A61M 1/36*    (2006.01)
    (Continued)

(52) U.S. Cl.
    CPC .............. *A61M 1/3653* (2013.01); *A61M 1/36* (2013.01); *A61M 1/3656* (2014.02);
    (Continued)

(58) Field of Classification Search
    CPC .............. A61M 5/1418; A61M 1/3656; A61M 2205/18; A61M 2209/08; A61M 39/08; F16G 11/00; F16L 3/01
    (Continued)

(56) References Cited

U.S. PATENT DOCUMENTS 4,406,042 A  *  9/1983  McPhee .......................... 24/130
5,642,817 A     7/1997  O'Brien
(Continued)

FOREIGN PATENT DOCUMENTS

DE          197 46 057 A1     4/1999
DE      10 2006 011 313 B3    5/2007
(Continued)

OTHER PUBLICATIONS

PCT International Search Report from PCT/EP2012/003231 mailed on Nov. 9, 2012.
Internatioanl Preliminary Report on Patentability (IPRP) and Written Opinion in PCT/EP2012/003231, dated Feb. 14, 2014.

*Primary Examiner* — Tatyana Zalukaeva
*Assistant Examiner* — Andrew J Mensh
(74) *Attorney, Agent, or Firm* — Kilyk & Bowersox, P.L.L.C.

(57) ABSTRACT

A device for fixing a segment of tubing in the form of a loop, for an apparatus by which a fluid is fed to or out from a patient via tubing, in particular for monitoring vascular access in extra-corporeal blood treatment, and a tubing and an arrangement for monitoring, each having the device for fixing the segment, are also described. The fixing of the segment includes a guiding piece and a securing piece. The guiding piece fixes intersecting portions of the segment which forms an eye, thereby forming a loop which contracts under a tractive stress. The securing piece fixes a portion of the segment forming the eye such that when the loop tightens, that portion of the segment does not slip through the guiding piece. Alternatively, intersecting portions of the segment are fixed in a loop only by a guiding piece formed as an annular body.

7 Claims, 5 Drawing Sheets

(51) Int. Cl.
   *A61M 5/14* (2006.01)
   *A61M 25/02* (2006.01)
   *A61M 39/28* (2006.01)
   *A61M 1/00* (2006.01)
   *F16L 3/01* (2006.01)
   *F16G 11/00* (2006.01)

(52) U.S. Cl.
   CPC .......... *A61M 5/1418* (2013.01); *A61M 25/02* (2013.01); *A61M 39/281* (2013.01); *A61M 2205/18* (2013.01); *F16G 11/00* (2013.01); *F16L 3/01* (2013.01)

(58) Field of Classification Search
   USPC ........................... 604/6.16, 322; 24/130, 518
   See application file for complete search history.

(56) References Cited

U.S. PATENT DOCUMENTS 6,105,218 A * 8/2000 Reekie ............................ 24/518
   2009/0082742 A1* 3/2009 Tully et al. ................... 604/323
   2009/0306574 A1* 12/2009 Kopperschmidt ........... 604/6.16

FOREIGN PATENT DOCUMENTS

EP        2 292 192 A1    3/2011
   FR          567 345 A     2/1924
   GB          813 918 A     5/1959

* cited by examiner

DEVICE AND METHOD FOR FIXING A SEGMENT OF TUBING, FOR AN ARRANGEMENT FOR MONITORING AN ACCESS TO A PATIENT

CROSS REFERENCE TO RELATED APPLICATIONS

The present application claims priority to U.S. Provisional Application Ser. No. 61/514,912, filed on Aug. 4, 2011, and claims priority to Application No. DE 10 2011 109 378.1, filed in the Federal Republic of Germany on Aug. 4, 2011, each of which is expressly incorporated herein in its entirety by reference thereto.

FIELD OF INVENTION

The present invention relates to a device and method for fixing a segment of tubing in the form of a loop, for an apparatus by which a fluid is fed to a patient or fed out from the patient via tubing, in particular for monitoring the vascular access in extra-corporeal blood treatment in which a patient's blood is fed to the patient via venous tubing which has a venous canula for the patient and is fed out from the patient via arterial tubing which has an arterial puncturing canula. In addition, the present invention also relates to tubing for feeding a fluid to a patient or for feeding a fluid out of a patient which has a device of this kind for fixing a segment of the tubing, and to an arrangement for monitoring the infeed of a fluid via tubing to a patient and/or the outfeed of a fluid from a patient, which arrangement has a device of this kind for fixing a segment of the tubing. The present invention also relates to a method of monitoring an access to a patient for feeding a fluid to and/or feeding a fluid out of the patient.

BACKGROUND INFORMATION

In the field of medical technology, there are a large number of known pieces of apparatus by which, via tubing, fluids can be fed to a patient or fluids can be fed out of the patient. Access is generally gained to the patient in this case by means of a catheter for introduction into organs of the body or by means of a canula or needle for puncturing vessels. It has to be ensured that there is proper access to the patient during examination or treatment. It is therefore necessary for the access to the patient to be monitored.

An application which makes particularly severe demands on the safety of the access to the vessel is extra-corporeal blood treatment in which blood is fed out of the patient via arterial tubing which has an arterial puncturing canula, the blood is conveyed through a dialyser, and is fed back to the patient via venous tubing which has a venous puncturing canula. Even though the access to the patient is regularly monitored by the hospital staff, there is basically a danger in this case of the venous puncturing canula slipping out of the patient's blood vessel unnoticed. Whereas if the arterial canula slips out this involves air being drawn into the arterial tubing, which results in a visual and/or optical alarm being given due to the detection of air by the machine and in the treatment being interrupted, the slipping-out of the venous canula, and the free flow of blood into the surroundings of which there is then a danger, cannot readily be detected. However, if the slipping-out of the venous canula is not detected immediately, the patient may exsanguinate.

There are a large number of different arrangements in the prior art for solving this problem. Some of these arrangements have recourse to safety arrangements which are present as standard in the blood treatment machines and cause an immediate interruption of the extra-corporeal circulation of blood if there is a vascular access which is not in a proper state. The safety arrangements which are present as standard in treatment machines are generally based on monitoring the pressure in the extra-corporeal blood circuit. However, it has been found in practice that the slipping-out particularly of the venous puncturing canula cannot be detected with sufficient reliability simply by monitoring the pressure in the extra-corporeal blood circuit. It is true that some known safety arrangements do have adequate sensitivity but they also react very sensitively to changes in the patient's position, which often results in false alarms. It is also a disadvantage that existing pieces of blood treatment apparatus cannot readily be retrofitted with the known monitoring arrangements and instead the retrofitting calls for a complicated and cost-intensive incursion to be made into the treatment apparatus.

International Patent Publication No. WO 2007/104350 A1 describes an easily operated arrangement which can be produced inexpensively and retrofitted at any time and which allows an access to a patient to be monitored safely and reliably. The monitoring of the access to the patient is based on the forming of a loop in the fluid-carrying tubing. It is assumed that slipping-out of the puncturing canula or the catheter is attributable to tractive forces being applied to the tubing. When the tubing is stressed in traction, the loop is necessarily pulled closed. This results in an increased pressure drop in the tubing and this is easy to detect.

Special fixing means are used to fix the tubing in the form of a loop. International Patent Publication No. WO 2007/104350 A1 describes two alternative embodiments which differ in that in one embodiment the fixing means are fixing pieces which are included loose with the tubing whereas in the other embodiment the fixing pieces are an integral part of the catheter for accessing the patient. The characteristic feature of the fixing pieces which are included loose is two eyes which are each used to receive a section of the tubing, the tubing being fixed in the form of a loop.

With the known fixing pieces, a section of the tubing can be fixed in the form of a loop which contracts under a tractive stress. It is a disadvantage however that the tractive force required for this is relatively high.

SUMMARY

An object underlying the present invention is to provide a device and a method for fixing a segment of tubing in the form of a loop with which the tractive forces required for the contraction of the loop can be reduced.

In a first alternative exemplary embodiment, the device according to the present invention and the method according to the present invention are based on the use of a combination of a guiding piece and a securing piece. By the guiding piece, the intersecting portions of the segment of tubing which forms an eye are fixed in such a way that the eye forms a loop which contracts under a tractive stress. By the securing piece, that portion of the segment of tubing forming the eye which is situated between the intersecting portions is fixed in such a way that, when the loop tightens, that portion of the segment of tubing forming the eye which is situated between the intersecting portions does not slip through the guiding piece.

The guiding piece and the securing piece may form one common part or may take the form of separate parts. The guiding piece takes the form of an annular body which encloses the intersecting portions of the segment of tubing forming an eye. The guiding piece does not have to take the form of an annular body. Basically, any shape which is other than circular, such for example as an ellipse or a rectangle, is a possibility. Preferably however the annular body is a circular annular body in which the intersecting portions of the segment of tubing forming an eye are guided loose.

If the tubing is stressed in traction, the loop contracts, the intersecting portions of the segment of tubing being guided loose in the annular body forming the guiding piece. What is advantageous is that, as the loop tightens, the annular body rotates around the intersecting portions of the segment of tubing. This greatly reduces the friction on the segment of tubing in the annular body and appreciably lower tractive forces are thus required to tighten the loop.

The loop contracts until the securing piece retains that portion of the securing piece of the segment of tubing which is situated between the intersecting portions of the loop. The segment of tubing is suddenly kinked as a result of this. This results in an appreciably increased pressure drop in the tubing, and this is easy to detect.

In a preferred exemplary embodiment, the annular body forming the guiding piece is so designed that the guiding piece can be folded open to allow the tubing to be inserted and can be closed again once the tubing has been inserted. This exemplary embodiment makes it easier for the guiding piece to be placed on the tubing in order to fix the eye formed by the segment of tubing in a loop. The annular body forming the guiding piece preferably comprises two part-pieces, with one end of the first part-piece and one end of the second part-piece being connected together to be movable and the other end of the first part-piece and the other end of the second part-piece being able to be connected together by latching or snapping in. An exemplary embodiment which is a particular preference envisages a film hinge for connecting the ends of the two part-pieces to be movable. The latching or snapping in connection and the movable connection between the two part-pieces should be such that the guiding pieces forms an annular body which in the closed state has a smooth surface over which the intersecting portions of the segment of tubing can slide when the loop contracts.

Rather than a guiding piece which can be folded open, what is also possible is a guiding piece taking the form of a continuous annular body. However, in this exemplary embodiment the guiding piece cannot be placed round the intersecting portions of the segment of tubing. To form the loop, a segment of the tubing which has been kinked is passed through the annular body forming the guiding piece in this exemplary embodiment.

For the securing piece for securing the segment of tubing in the guiding piece, the present invention envisages two alternative exemplary embodiments.

In one exemplary embodiment, the securing piece takes the form of an annular body which encloses the portion of the segment of tubing forming an eye. To allow the tubing to be inserted, the securing piece too may be able to be folded open and may be designed to be able to be closed again once the tubing has been inserted. Basically however, it is also possible for a securing piece taking the form of a continuous annular body to be drawn onto the tubing even before the guiding piece is fitted.

In an alternative exemplary embodiment, the securing piece takes the form of an elongated body, with the ends of the elongated body forming the securing piece being fastened to the annular body forming the guiding piece in such a way that the ends of the elongated body can be displaced along the annular body forming the securing piece.

In the first alternative exemplary embodiment, the annular body forming the securing piece, which encloses the loop loosely, is not connected to the annular body forming the guiding piece, whereas in the second alternative exemplary embodiment, the elongated body forming the securing piece is connected to the annular body forming the guiding piece. In both exemplary embodiments, the securing piece prevents the loop from being pulled completely through the guiding piece. In the first exemplary embodiment, the annular body forming the securing piece is simply carried along with the loop as it contracts, whereas in the second exemplary embodiment, the annular body forming the securing piece is able to rotate freely in the guiding piece, or vice versa, thus not preventing the loop from contracting.

The securing piece taking the form of an elongated body is preferably not connected to the annular body forming the guiding piece until the segment of tubing forms the loop. A preferred exemplary embodiment therefore makes provision for at least one of the two ends of the elongated body forming the securing piece to be detachably fastened to the annular body forming the guiding piece. Preferably it is both ends of the elongated body forming the securing piece which are detachably fastened to the annular body forming the guiding piece, thus enabling the guiding piece to be completely removed from the securing piece and the securing piece not to get in the way when the loop is being formed. Basically however, it is equally possible for the securing piece not to be able to be detached from the guiding piece.

However, in this case it is necessary for one or both ends of the tubing to be drawn through the guiding piece on both sides of the securing piece in order to form the loop.

In a second alternative exemplary embodiment, the device according to the present invention and the method according to the present invention are based on the use of only one guiding piece. In the first alternative exemplary embodiment, the ends of the segment of tubing extend through the guiding piece taking the form of an annular body from the same side, whereas in the second alternative exemplary embodiment, the ends of the segment of tubing extend through the guiding piece taking the form of an annular body from sides which are opposite from one another. Because the loop is unable to pull itself through the guiding ring when the loop contracts in the second exemplary embodiment, a securing piece as used in the first alternative exemplary embodiment is not necessary.

An apparatus for feeding liquid to or out of a patient can be retrofitted with the device according to the present invention at any time.

Known pieces of blood treatment apparatus already have a device for monitoring the pressure in the extra-corporeal blood circuit. If the pressure exceeds preset limits, the blood treatment apparatus is able to give an alarm and/or interrupt the blood treatment. The mechanical device required for this purpose is present in the known pieces of blood treatment apparatus. All that is therefore necessary is for the preset limiting values for the pressure in the extra-corporeal blood circuit to be matched to the tubing being used.

It is an advantage not only that a faulty access to a patient can easily be detected but also that the forming of a loop can, as it were, weaken the transmission of tractive forces to the catheter or canula. If the tubing is stressed in traction, the loop first tightens, and the tractive forces are thus not transmitted to the catheter or canula immediately. Only when the loop has tightened sufficiently for the tubing to kink are the tractive forces transmitted to the catheter or canula. That however is the point at which the protective mechanism already goes into action. All that is needed is a slight kink to enable an increase in the pressure drop in the tubing to be detected reliably. It is also advantageous that the back pressure builds up more quickly as the speed of flow of the fluid increases. This is particularly the case when the tubing is composed of a flexible material which yields easily.

If the length of the tubing is of suitably generous dimensions and the patient is allowed a certain freedom of movement, only a few false alarms will occur because no tractive forces, or only small ones, can be exerted on the tubing within the scope of ordinary movements. It is also possible for the apparatus for feeding the fluid in or out not to switch off immediately in the event of a fault but merely to trigger an alarm. Should alarms be triggered, the hospital staff can remove the kink by returning the tubing to its looped form without the treatment having to be interrupted.

Basically it would be possible for the blood tubing easily to be set up as an eye, and for one of the two free ends of the tubing easily to be passed through the eye, thus enabling the loop to tighten under a tractive load, without any other aids. It has been found in the case of the commercially available blood tubing that unintentional kinking of the blood tubing may occur even when a free end of the tubing is being passed through such an eye, which would mean that the blood tubing could no longer be used for the dialysis treatment because of this. It has also been found that considerably higher tractive forces than are the case with the present invention would be needed to tighten a loop made in this way under a tractive load, due to the high friction between the portions of the blood tubing which rest directly against one another which occurs with the usual materials for blood tubing. There is thus a danger that the canula will slip out of the patient's fistula or shunt under a tractive load before the loop is able to tighten. However, in accordance with the present invention, even low tractive forces are intended to cause the loop to tighten. The disadvantages mentioned are overcome by the present invention without the need for new blood tubing to be developed, which would involve the disadvantages mentioned and in particular premature kinking and high friction.

Exemplary embodiments of the present invention will be described in detail with reference to the accompanying drawings.

DETAILED DESCRIPTION

Figure 1:
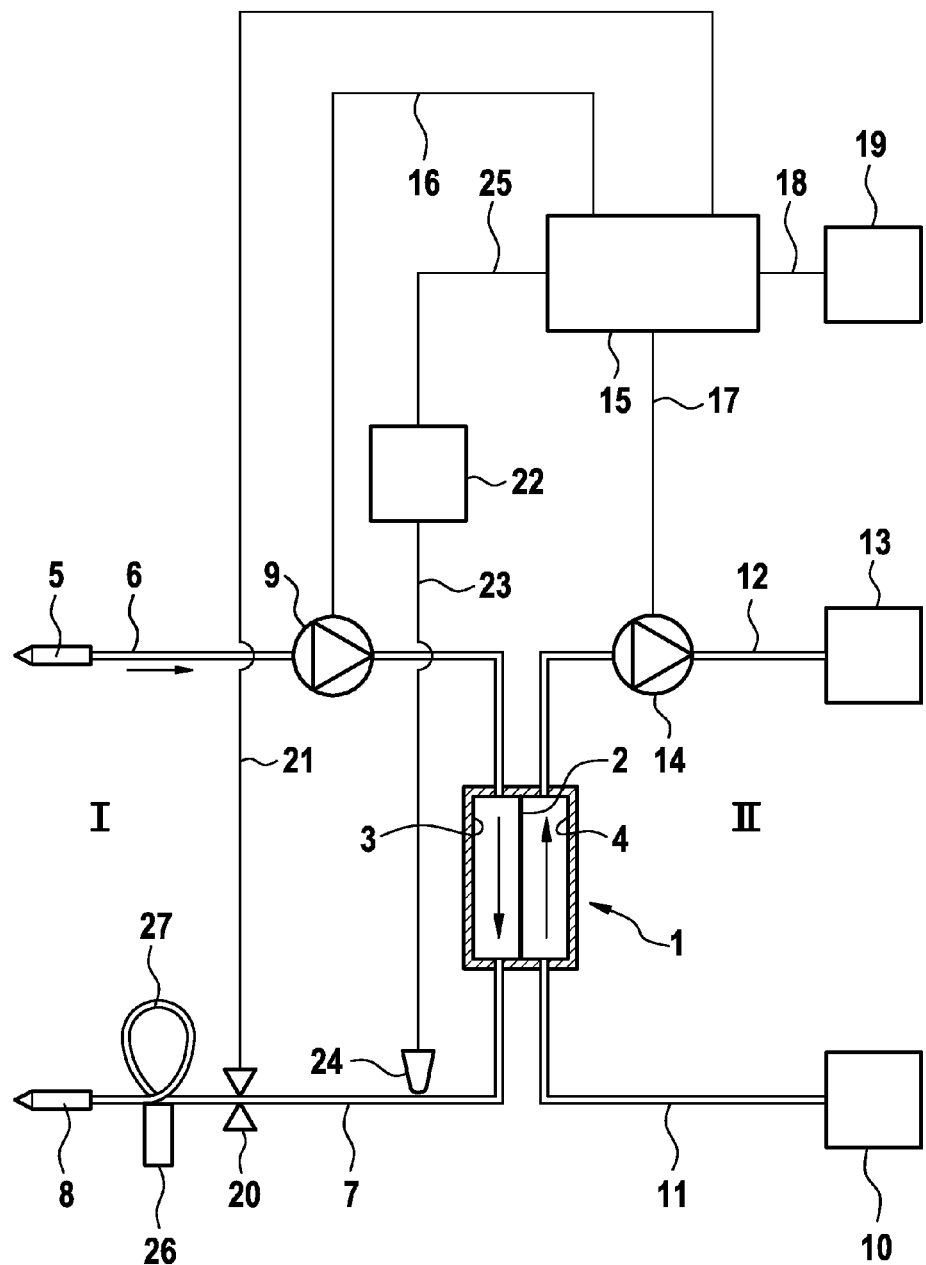
FIG. 1 is a highly simplified schematic view of the main components of a blood treatment apparatus, together with the arrangement according to the present invention for monitoring the access to the patient.

FIG. 1 shows the main components of a haemodialysis apparatus which has an arrangement for monitoring the venous vascular access. The haemodialysis apparatus has a dialyser 1 which is divided by a semi-permeable membrane 2 into a blood chamber 3 and a dialysis-fluid chamber 4. Arterial tubing 6, which runs to the inlet of the blood chamber 3 of the dialyser, is connected to the patient's fistula or shunt by means of an arterial puncturing canula 5. Running from the outlet of the blood chamber 3 of the dialyser 1 is venous tubing 7 which is connected to the patient's fistula or shunt by means of a venous puncturing canula 8.

The arterial tubing 6 is inserted in an occluding blood pump 9 which pumps the blood in the extra-corporeal blood circuit I.

The dialysis-fluid circuit II of the haemodialysis apparatus comprises a source 10 of dialysis fluid to which is connected a dialysis-fluid infeed line 11 which runs to the inlet of the dialysis-fluid chamber 4 of the dialyser. Running from the outlet of the dialysis-fluid chamber 4 of the dialyser 1 is a dialysis-fluid outfeed line 12 which runs to an outlet 13. A dialysis-fluid pump 14 is connected into the dialysis-fluid outfeed line 12. Control of the dialysis apparatus is the responsibility of a central control unit 15 which operates the blood and dialysis-fluid pumps 9, 14 by means of control lines 16, 17. The central control unit 15 is connected by a data line 18 to an alarm unit 19 which gives a visual and/or audio alarm in the event of a fault.

Downstream of the blood chamber 3 of the dialyser 1, on the venous tubing 7, there is an electromagnetically actuatable tube clamp 20 which is closed by the central control unit 15, via a further control line 21, should the venous puncturing canula (needle) slip out of the patient's vascular access due to a tractive force on the tubing. As well as this, the control unit 15 also stops the blood pump 9 on the canula slipping out.

To monitor the pressure in the venous tubing 7, the dialysis apparatus has a monitoring device 22 which is connected by a data line 23 to a pressure sensor 24 which measures the pressure in the venous tubing 7. The pressure monitoring device 22 communicates with the central control unit 15 via a further data line 25.

The arrangement for monitoring the venous vascular access has the device 26 which will be described in detail below for fixing a segment of the venous tubing 7 in the form of a loop 27. The loop is formed upstream of the venous puncturing canula 8, preferable in a portion of the tubing in which the tubing is still lying on the patient's body, such for example as on his lower arm.

The venous tubing 7 is not stressed in traction during the dialysis treatment. The pressure monitoring device 22 measures the pressure P in the venous tubing, which is within preset limits. Typical venous pressures are approximately 100 to 200 mm Hg. Let it be assumed that the pressure monitoring device 22 is measuring a venous pressure of 150 mm Hg. Under pressure conditions of this kind, a window 100 mm Hg wide is defined between the limiting values, the lower limiting value for pressure being 100 mm Hg and the upper limiting value being 200 mm Hg. If the pressure measured is above or below the preset limits of 100 and 200 mm Hg respectively, the central control unit 15 triggers a visual and/or audio alarm.

If there is a pull on the venous tubing 7 upstream of the loop 27, there is a danger of the puncturing canula 8 slipping out of the patient's vein. If this is not noticed, there is a threat to the patient's life. However, the fall in pressure in the venous tubing due to the loss of back pressure of approximately 15 to 25 mm Hg at the access to the patient is unable to produce a drop below the lower limiting value of 100 mm Hg for the venous pressure, which means that without the monitoring arrangement according to the present invention, the slipping-out of the venous puncturing canula would not be noticed.

However, because the tubing forms a loop above the puncturing canula, the slipping-out of the puncturing canula results, due to a tractive force on the tubing, in an alarm being triggered and/or in the blood treatment being interrupted. If there is a pull on the venous tubing 7, the loop 27 first contracts, thus enabling the tractive stress to be "absorbed" initially. However, further tractive stress results in the loop contracting until the tubing finally kinks Because the blood backs up at the kink, the venous pressure in the tubing upstream of the kink rises. The back pressure depends on the cross-section of the kinked segment of tubing which remains open at the kink and on the flowrate of the blood. Using the pressure sensor 24 arranged upstream of the loop 27, the pressure monitoring device 22 measures the pressure upstream of the kink. Within a short time, approximately 1 to 2 seconds, there is a sharp rise in the pressure of 150 mm Hg due to the constriction at the kinked point, as a result of which it rises above the upper limiting value of 200 mm Hg for the venous pressure. Consequently, the central control unit 15 triggers an alarm and interrupts the blood treatment by closing the venous tube clamp 20 and stopping the blood pump 9.

Various limiting values may be preset at different levels in the control system for the purposes of the monitoring. If for example the pressure measured exceeds a first preset limiting value, it can be concluded that the loop has partly contracted and the puncturing canula is probably slipping out, and a pre-alarm can be triggered. If for example the pressure measured exceeds a second limiting value which is higher than the first limiting value, it can be concluded that the tubing is kinked and there is a danger of the puncturing canula slipping out of the access to the patient.

Because any appreciable change in pressure as the loop tightens does not occur until relatively late, i.e., only when the kinking occurs, it has to be ensured that the tubing will in fact kink. Because an assured overrun of the upper limit on the pressure measured occurs as a result of the kinking of the tubing, but in conventional tubing this kinking only occurs when the tightening of the loop is well advanced, it may be advantageous for early kinking to be encouraged. The sensitivity of the monitoring device can be increased in this way. It is advantageous for this to be assisted by means of a designed-in or structural anisotropy for the tubing, the shape and/or characteristics of the material of the tubing at the kinking point being changed to differ from the shape and/or characteristics of the material away from the kinking point. In this way, an intended kinking point may for example be created by making the wall of the tubing thinner or for example by causing its cross-sectional shape to be other than circular. In this way, the circular tubing may for example be of elliptical cross-section at the kinking point.

In what follows, there will be described a first exemplary embodiment of the device 26 for fixing a segment of the tubing in the form of a loop, which device 26 can be mounted at any time on existing tubing belonging to a conventional dialysis machine or may already be present on the tubing of the dialysis machine. Because known dialysis machines generally already have a device for monitoring pressure which reacts when there is a rise above and/or a fall below preset limiting values, no further arrangements need be provided to enable the access to the patient to be monitored.

Figure 2:
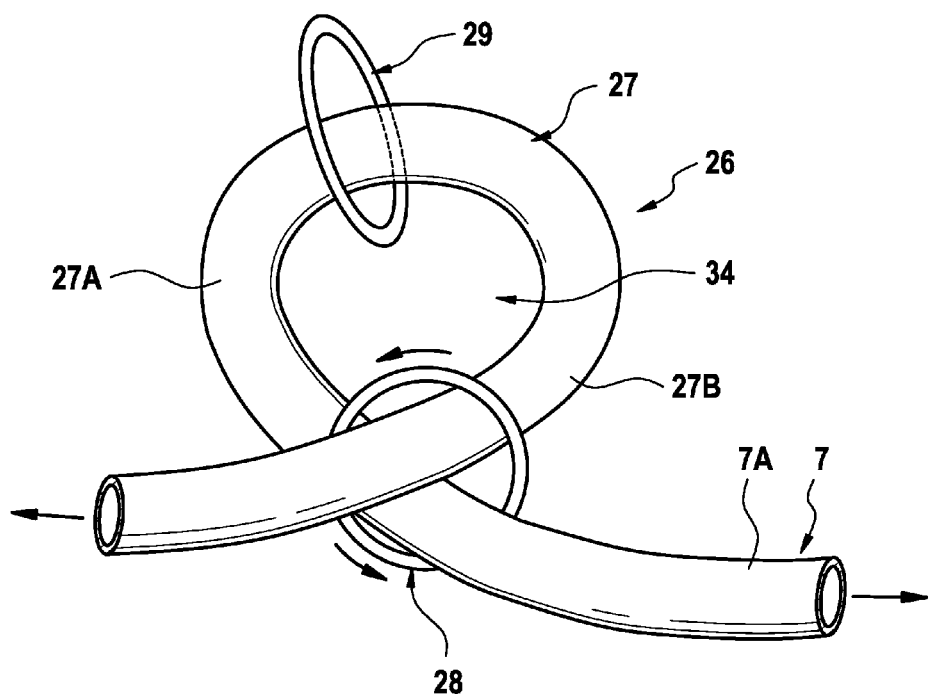
FIG. 2 shows a first exemplary embodiment of the device according to the present invention for fixing a segment of one of the tubing lines of the blood treatment apparatus of FIG. 1, the tubing being shown before the loop contracts.

The device 26 for fixing a segment of the tubing 7 in the form of a loop 27 (FIG. 1) comprises a guiding piece 28 and a securing piece 29 (FIG. 2). In the first exemplary embodiment, both the guiding piece 28 and the securing piece 29 take the form of annular bodies. In the present exemplary embodiment, the guiding piece 28 and securing piece 29 are circular annular bodies, which will be referred to below in the case of this exemplary embodiment as the guiding ring 28 and securing ring 29.

Figure 3:
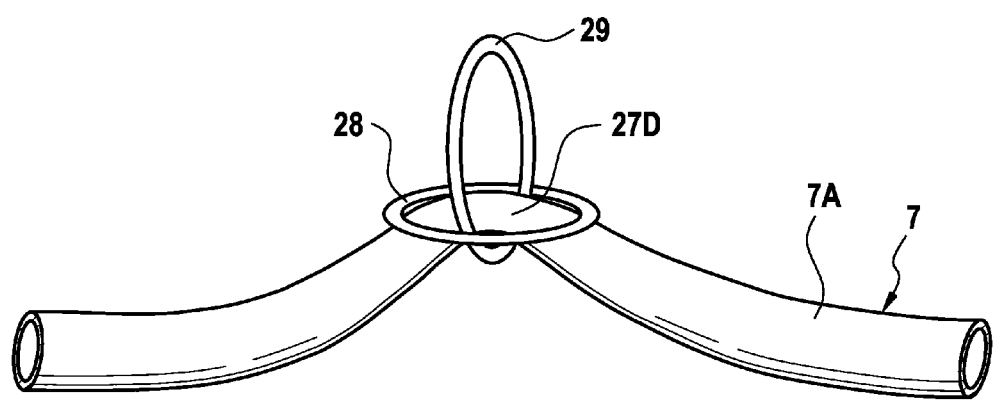
FIG. 3 shows the device for fixing a segment of tubing of FIG. 2, the loop in the tubing having been tightened.

FIG. 2 shows the guiding ring 28 and securing ring 29 together with the segment 7A of the tubing 7 which is fixed in the form of a loop 27. The segment 7A of the tubing 7 forms an eye 34 and the guiding ring 28 fixes the intersecting portions 27A, 27B of the segment 7A in such a way that the loop 27 is formed. If one or both ends of the tubing 7 are pulled, the loop 27 contracts. The securing ring 29 prevents the loop 27, when it contracts under a tractive stress, from slipping through the guiding ring 28. As well as this, the securing ring 29 also causes the tubing to kink under tractive stress, meaning that there is an easily detected change in pressure due to the kinked point 27D. The kinked segment 7A of the tubing 7 is shown in FIG. 3 together with the guiding and securing rings 28, 29.

As the loop 27 tightens, the intersecting portions 27A, 27B of the segment 7A of the tubing 7 are guided and fixed by the guiding ring 28. While the loop 27 contracts, the guiding ring 28 rotates around the intersection 27A, 27B in the tubing. This considerably reduces the friction on the segment of tubing in the guiding ring. The loop 27 tightens until the securing ring 29 is resting against the guiding ring 28. When this is the case the securing ring and guiding ring make an angle of approximately 90°. The kinked point 27D which is produced lies in the centre of the guiding ring 28 above the securing ring 29. Because the securing ring 29 encloses the segment of tubing loosely as the loop contracts, the securing ring 29 does not prevent the segment of tubing from contracting. The tractive force required to contract the loop is therefore small.

For operation with particularly little friction, the inside diameter of the guiding ring 28 should preferably be somewhat larger than twice the outside diameter of the tubing 7. The device according to the present invention is preferably mounted on those portions of the tubing lines used in dialysis which are situated at the canulas. The outside diameter of these portions of the tubing is typically 5.5 mm. With tubing of this kind, a guiding ring having an inside diameter of approximately 14 mm has proved to be advantageous. The inside diameter of the guiding ring should preferably be between 10 and 20 mm. A thickness d for the guiding ring of 1-2 mm, and in particular of 1.5 mm, has proved advantageous in this case.

The outside diameter of the securing ring 29 should preferably be of a size such that the securing ring 29 cannot be pulled through the guiding ring 28 when the loop 27 contracts. It has proved to be advantageous for the outside diameter of the securing ring 29 to be somewhat larger than the outside diameter of the guiding ring 28. What has also proved to be advantageous is for the thickness of the securing ring 29 to be somewhat greater than the thickness of the guiding ring 28. The surfaces of the guiding ring 28 and the securing ring 29 should preferably be of as smooth a nature as possible, thus enabling the tubing to slide in the rings 28, 29.

Figure 4:
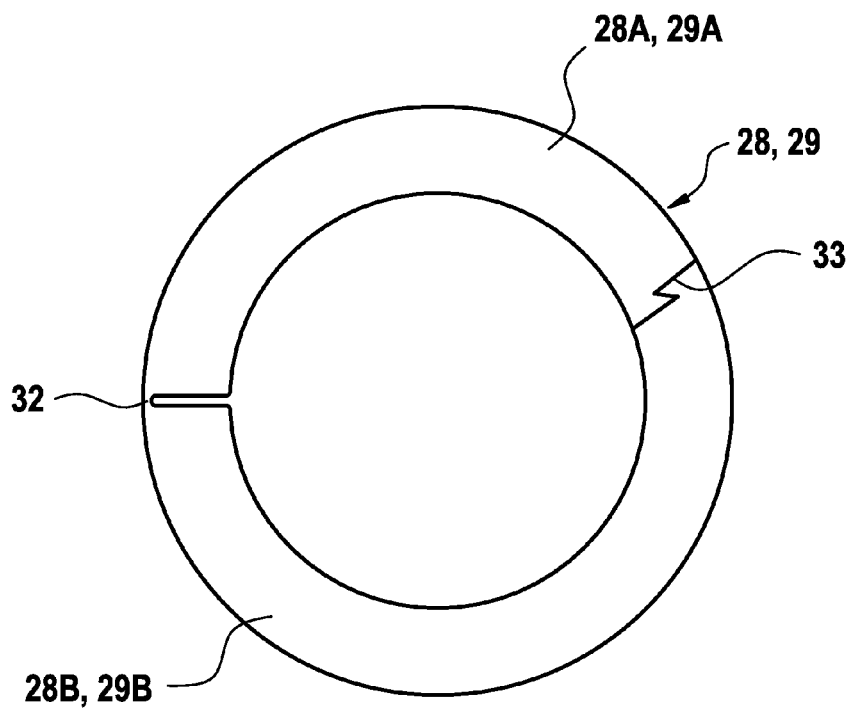
FIG. 4 is a plan view of the guiding piece or securing piece of the device for fixing the tubing.
Figure 5:
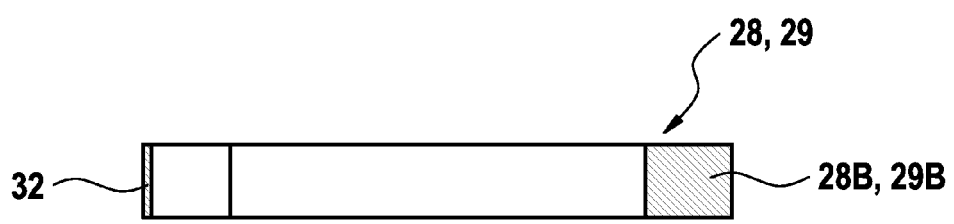
FIG. 5 is a view in section of the guiding piece or securing piece of FIG. 4.

FIGS. 4 and 5 show an exemplary embodiment which is particularly preferred and in which both the guiding ring 28 and the securing ring 29 may take the form. The advantage of this exemplary embodiment lies in the fact that the guiding or securing ring 28, 29 does not have to be drawn onto the tubing, or the tubing does not have to be drawn through the ring, and instead the ring can be placed around the tubing. The guiding and securing rings 28, 29 comprise two part-pieces 28A, 29A and 28B, 29B respectively. One end of the first part-pieces 28A, 29A and one end of the second part-pieces 28B, 29B are connected together by a hinge 32, and in particular a film hinge, which is merely schematically indicated in FIGS. 4 and 5. The other ends of the two part-pieces are connected together by a latching or snap-action joint 33 which is likewise merely schematically indicated. On the latching or snap-action joint 33 being released, the guiding ring or securing ring 28, 29 can thus be folded open and placed around the tubing 7.

If both the guiding ring and the securing ring 28, 29 are able to be folded open, the tubing only needs to be formed into an eye and the securing ring 29 fitted.

If the guiding ring 28 is a continuous ring and the securing ring 29 is a ring which can be folded open, the tubing is first kinked. The kinked part of the tubing is then passed through the continuous guiding ring. The securing ring 29, having been folded open, is then placed around the tubing and closed. If both the rings 28, 29 are continuous rings, the tubing has to be pulled through both rings, thus forming a loop (FIG. 2).

The rings 28, 29 should preferably be mounted on the tubing after the canula has been inserted at the beginning of the dialysis treatment and should not be removed again until the end of the dialysis treatment. The rings should be mounted on that part of the tubing to which the dialysis canula is connected, because the tubing connected to the dialysis is thinner and thus more flexible than that of the system of blood tubing which is connected.

Figure 6:
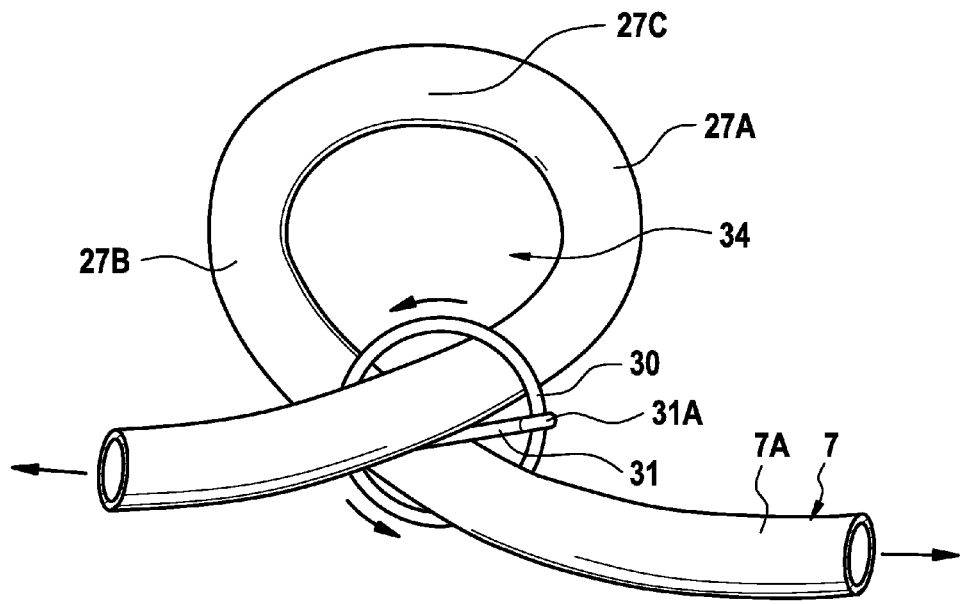
FIG. 6 shows an alternative exemplary embodiment of the device according to the present invention for fixing a segment of one of the tubing lines of the blood treatment apparatus of FIG. 1, the tubing being shown before the loop contracts.
Figure 7:
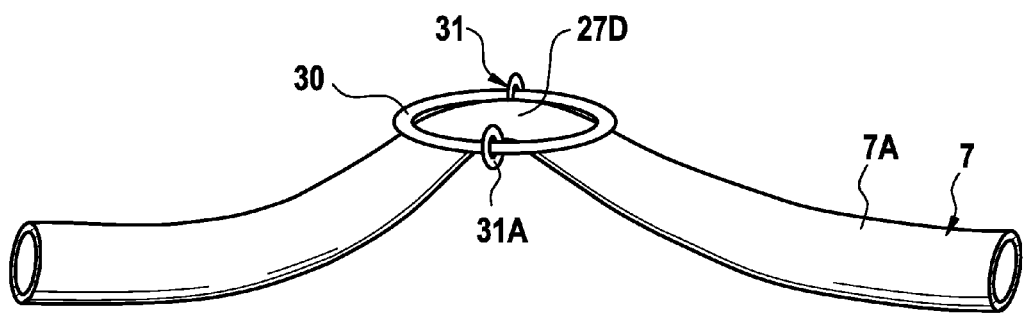
FIG. 7 shows the device for fixing a segment of tubing of FIG. 6, the loop in the tubing having been tightened.

FIGS. 6 and 7 show an alternative exemplary embodiment of the device for fixing a segment of tubing in the form of a loop, before and after the contraction of the loop. The alternative exemplary embodiment too has a guiding piece 30, which is once again a guiding ring 30 in the alternative exemplary embodiment. The alternative exemplary embodiment differs only in the form taken by the securing piece 31. In the alternative exemplary embodiment, the securing piece 31 takes the form of an elongated body which is fastened to the guiding ring 30.

Figure 8:
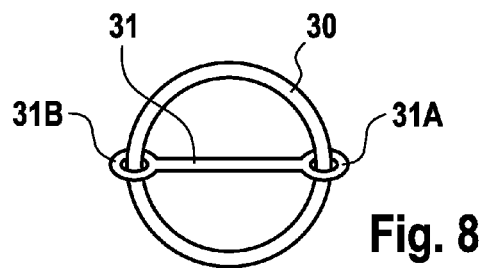
FIG. 8 shows a variant of the alternative exemplary embodiment of the device for fixing a segment of tubing.

In the present exemplary embodiment, the securing piece is a bridge 31 whose two ends 31A, 31B are displaceably fastened to the guiding ring 30 (FIG. 8). The two ends 31A, 31B of the securing bridge 31 may for example take the form of strips which loosely enclose the guiding ring 30. The securing bridge 31 divides the guiding ring 30 into two halves in this case, through which the intersecting portions 27A, 27B of the segment 27 of tubing extend.

It is of advantage if one or both ends 31A, 31B of the securing bridge 31 are releasably connected to the guiding ring 30. Any of the connections familiar to the person skilled in the art are available as releasable connections. If both ends 31A, 31B of the securing bridge 31 are releasably connected to the guiding ring 30, the securing bridge 31 can be completely removed. If one only of the two ends of the securing bridge 31 is releasably connected to the guiding ring 30, the securing bridge 31 can be folded over sideways. The fitting of the securing ring is simplified in both cases.

The length of the securing bridge 31 corresponds to the diameter of the guiding ring 30. Because the securing bridge 31 is loosely guided, the guiding ring 30 is able to rotate as the loop 27 contracts whereas the guiding bridge maintains its position between the intersecting portions 27A, 27B of the segment 27 of tubing, or vice versa. The loop 27 tightens under tractive stress until the segment 27C of tubing which is situated between the intersecting portions 27A, 27B is pulled up against the securing bridge 31, as a result of which the tubing kinks at the kinked point 27D (FIG. 7).

The device can be fitted easily by first removing or folding over the securing bridge 31 and drawing the kinked part of the tubing 27 through the guiding ring 30. The securing bridge is then fitted to the guiding ring. To do this, either both or only one of the two ends 31A, 31B of the guiding bridge 31 are releasably connected to the securing ring.

Basically, the guiding bridge 31 may take different forms. It is of advantage if the guiding bridge 31 is narrow in the circular plane of the guiding ring 30 in order not to reduce the size of the semi-circular areas in which the loop of tubing is guided to an excessive degree. In the longitudinal direction of the tubing, the bridge should take a wider form to ensure that the tubing kinks. The guiding bridge should always be given a profile such that any damage to the tubing as it kinks is prevented.

The guiding and securing pieces 28, 29 and 30, 31 may take the form of a product intended to be used once only. Plastics materials of fairly high strength, e.g., polycarbonate or polyoxymethylene, are an obvious choice in this case. To rule out the possibility of a product intended to be used once only being re-used, the latching and snap-action joint 33 of the securing piece or guiding piece may be so designed that the two part-pieces can only be connected together once. Suitable connecting mechanisms are known to the person skilled in the art. If the guiding and securing pieces are intended to be re-usable, the guiding and securing pieces may be composed of stainless steel. Stainless steel is an obvious choice particularly for the guiding piece because of its high strength.

Figure 9:
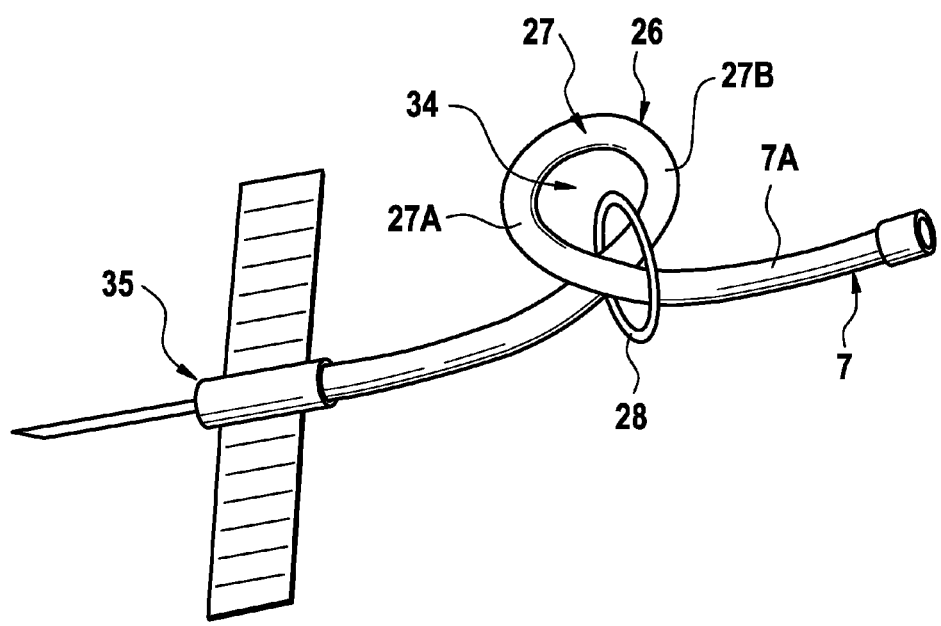
FIG. 9 shows an alternative exemplary embodiment of the device according to the present invention for fixing a segment of one of the tubing lines of the blood treatment apparatus of FIG. 1.

FIG. 9 shows an alternative exemplary embodiment of the device according to the present invention for fixing a segment of one of the tubing lines of the blood treatment apparatus shown in FIG. 1. The alternative exemplary embodiment differs from the exemplary embodiments which have been described by reference to FIGS. 2 to 8 in that the alternative exemplary embodiment does not have a securing piece but only a guiding piece 28 to fix a segment of the tubing. Parts which correspond to one another have been given the same reference numerals. FIG. 9 shows the segment 7A of the tubing 7 to which the puncturing canula 35 is fastened. Also situated on this segment 7A of tubing is the guiding piece 28 taking the form of an annular body. The two ends of the segment of tubing are passed through the guiding piece 28 from the two sides, as a result of which that section of the segment of tubing which forms an eye 34 is fixed in a loop 27 which contracts under tractive stress. The guiding piece 28 encloses the intersecting portions 27A, 27B of the segment of tubing loosely. The loop 27 cannot be pulled through the guiding piece 28 in this case because the guiding piece acts as the securing piece at the same time.

What is claimed is:

1. An arrangement for monitoring at least one of an infeed of a fluid via tubing to a patient or an outfeed of the fluid from the patient, the monitoring arrangement comprising:
   a device configured to monitor a pressure in the tubing such that if there is a change in pressure that exceeds a preset limiting value due to a tractive stress on the tubing, it is concluded that a cannula on the tubing is slipping out;
   a guiding piece taking a form of an annular body configured to loosely fix intersecting portions of a segment of the tubing which forms an eye, which intersecting portions pass through a same opening of the guiding piece, the eye forming a loop which contracts under the tractive stress; and
   a securing piece configured to fix a portion of the segment of tubing forming the eye which is situated between the intersecting portions, such that the portion of the segment of tubing forming the eye which is situated between the intersecting portions is kinked and does not slip through the guiding piece when the loop tightens.

2. A method of monitoring an access to a patient for at least one of an infeed of a fluid to or an outfeed of a fluid from a patient via tubing, the method comprising:
   monitoring a pressure in the tubing;
   fixing in a loop, by a guiding piece taking a form of an annular body, a segment of the tubing which forms an eye, the guiding piece enclosing intersecting portions of the segment of tubing which forms the eye;
   drawing a kinked segment of the tubing through the guiding piece, the eye being fixed by the guiding piece; and
   fixing, by a securing piece, a portion of the segment of tubing forming the eye which is situated between the intersecting portions such that when the loop tightens, the portion of the segment of tubing forming the eye which is situated between the intersecting portions does not slip through the guiding piece.

3. The method according to claim 2, wherein the portion of the segment of tubing forming the eye which is situated between the intersecting portions is secured against slipping out of the guiding piece by the securing piece taking a form of an annular body which is placed around the portion of the segment of tubing forming the eye which is situated between the intersecting portions.

4. The method according to claim 2, wherein the portion of the segment of tubing forming the eye which is situated between the intersecting portions is secured against slipping out of the guiding piece by the securing piece taking a form of an elongated body whose two ends are fastened to the guiding piece such that the ends of the elongated body are displaceable along the guiding piece.

5. The arrangement according to claim 1, wherein:
   the fluid is a patient's blood;
   the tubing comprises venous tubing and arterial tubing; and
   the arrangement monitors a vascular access in an extracorporeal blood treatment in which the patient's blood is fed to the patient via the venous tubing which has a venous puncturing cannula and is fed out from the patient via the arterial tubing which has an arterial puncturing cannula.

6. The arrangement according to claim 1, wherein the securing piece is an annular body.

7. The arrangement according to claim 1, wherein the securing piece is an elongated body whose two ends are fastened to the guiding piece such that the ends of the elongated body are displaceable along the guiding piece.

* * * * *